(12) United States Patent
Otsubo

(10) Patent No.: US 6,368,312 B1
(45) Date of Patent: Apr. 9, 2002

(54) DISPOSABLE PULL-ON DIAPER

(75) Inventor: Toshifumi Otsubo, Kagawa-ken (JP)

(73) Assignee: Uni-Charm Corporation (JP)

( * ) Notice: Subject to any disclaimer, the term of this patent is extended or adjusted under 35 U.S.C. 154(b) by 0 days.

(21) Appl. No.: 09/410,224

(22) Filed: Sep. 30, 1999

(30) Foreign Application Priority Data

Sep. 30, 1998 (JP) .......................................... 10-278343

(51) Int. Cl.$^7$ ................................................ A61F 13/15
(52) U.S. Cl. ................................ 604/385.01; 604/385.3
(58) Field of Search ............................ 604/396, 385.23, 604/385.01, 385.21, 385.22, 385.24, 385.3, 385.14, 385.16

(56) References Cited

U.S. PATENT DOCUMENTS

| | | |
|---|---|---|
| 4,578,066 A | 3/1986 | O'Conner |
| 4,610,681 A * | 9/1986 | Strohbeen et al. .......... 604/369 |
| 5,137,526 A | 8/1992 | Coates |
| 5,185,011 A | 2/1993 | Strasser |
| 5,324,278 A | 6/1994 | Visscher et al. |
| 5,575,782 A | 11/1996 | Hasse et al. |
| 5,593,400 A | 1/1997 | O'Leary |
| 5,626,571 A | 5/1997 | Young et al. |
| 5,846,232 A | 12/1998 | Serbiak et al. |

FOREIGN PATENT DOCUMENTS

| | | |
|---|---|---|
| EP | 0 226 789 A | 7/1987 |
| EP | 0 763 353 A2 | 3/1997 |
| EP | 0 933 073 A2 | 8/1999 |
| GB | 2 242 821 A | 10/1991 |
| WO | WO 99/07319 | 2/1999 |

OTHER PUBLICATIONS

Copy of European Search Report completed Feb. 13, 2001.

* cited by examiner

Primary Examiner—John G. Weiss
Assistant Examiner—Jamisue Webb
(74) Attorney, Agent, or Firm—Baker & Daniels

(57) ABSTRACT

A disposable pull-on diaper includes a liquid absorbent core, and the core is joined to a topsheet in front and rear waist regions as well as in a crotch region but not joined to a backsheet in the front and rear waist regions. The topsheet and the backsheet are not joined to each other in their portions extending between longitudinally opposite ends of the liquid-absorbent core and a peripheral edge of a waist-opening. The diaper thus constructed prevents the core from being flexed or crooked.

3 Claims, 4 Drawing Sheets

1

DISPOSABLE PULL-ON DIAPER

BACKGROUND OF THE INVENTION

This invention relates to a disposable pull-on diaper for absorption and containment of bodily wastes.

A disposable pull-on diaper is well known, which comprises a liquid-pervious topsheet, a liquid-impervious backsheet and a liquid-absorbent core disposed between these two sheets. These components are assembled together to form a waist-opening and a pair of leg-openings. FIG. 4 in the accompanying drawings is a sectional view showing an example of such well-known diaper. As shown, front and rear waist regions 106, 107 of a diaper 100 are put flat together and joined to each other along their respective side edges so as to form a waist-opening 111 and a pair of leg-openings 112, thereby to present a pants-like or brief configuration. Both the waist-opening 111 and the leg-openings 112 are provided along their peripheral edges with elastic members 113, 114, respectively, extending circumferentially and secured under appropriate tension thereto. FIG. 5 is a view similar to FIG. 4, showing the same well-known diaper as the elastic members 113, 114 have contracted. Referring now to FIGS. 4 and 5, movements of the diaper components before and after the elastic; members 114 for the leg-opening have contracted will be described with respect to the uppermost point 121 of the leg-opening 112. As will be apparent from this comparison, contraction of the members 114 causes a crotch region 108 of the diaper 100 to move upward together with a liquid-absorbent core 102. However, topsheet 103 and the backsheet 104 are joined to teach other by means of hot melt adhesive 116, 116A, provided at front and rear ends of the topsheet 103 and the backsheet 104 and provided immediately above front and rear ends 119, 120 of the liquid-absorbent core 102. Such arrangement disadvantageously restricts the liquid-absorbent core 102 against freely moving upward and, in consequence, forcibly crook the liquid-absorbent core 102 as seen in FIG. 5.

Once such crookedness occurring in the liquid-absorbent core has become permanent, a gap is left due to the permanent crookedness between the diaper put on the wearer's body and the wearer's skin. Such gap makes it difficult for the liquid-absorbent core to absorb body fluids discharged on the diaper as rapidly as possible. Furthermore, the crookedness of the liquid-absorbent core increases an apparent thickness of the diaper and makes the packaged diaper inconveniently bulky.

SUMMARY OF THE INVENTION

It is an object of the present invention to provide a disposable pull-on diaper having a liquid-absorbent core that is free from crookness or deformation.

According to the present invention, there is provided a disposable pull-on diaper having a front region, a rear region and a crotch region therebetween, the diaper comprising a liquid-absorbent core, a topsheet overlying the liquid-absorbent core and a backsheet underlying the liquid-absorbent core, the liquid-absorbent core extending across the crotch region into the front and rear waist regions, the front and rear waist region being joined to each other along side edges thereof to form a waist-opening and a pair of leg-openings; the waist-region and the leg-openings being provided with elastic members secured under tension thereto and extending circumferentially along peripheral edges of the respective openings; and the topsheet and the backsheet being joined to each other along the peripheral edges of the respective openings.

In such disposable pull-on diaper, the liquid-absorbent core has front and rear ends adjacent outer ends of the front and rear waist regions, respectively, defining together the peripheral edge of the waist-opening so that the liquid-absorbent core is restrained against a movement thereof relative to the topsheet in the front and rear waist regions as well as in the crotch region but freely movable relative to the backsheet at least in the front and rear waist regions; and the topsheet and the backsheet are not joined to each other at portions thereof extending outward beyond the front and rear ends of the liquid-absorbent core to the peripheral edge of the waist-opening.

According to one embodiment of the present invention, a portion of the topsheet extending outward beyond any one of the front and rear ends of the liquid-absorbent core to the peripheral edge of the waist-opening is tucked between the liquid-absorbent core and the backsheet.

DETAILED DESCRIPTION OF THE PREFERRED EMBODIMENTS

Details of a disposable pull-on diaper according to the present invention will be more fully understood from the description given hereunder with reference to the accompanying drawings.

Figure 1:
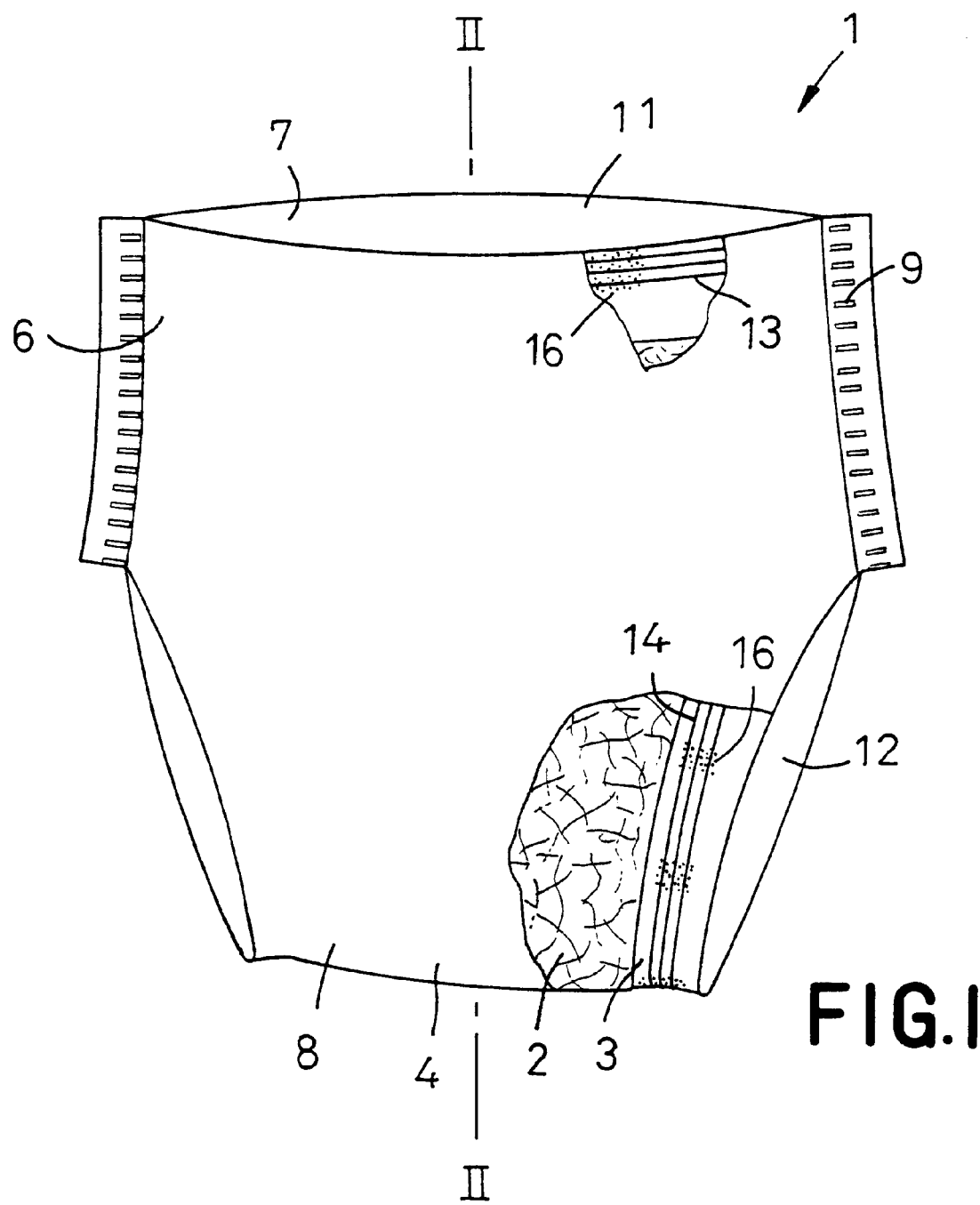
FIG. 1 is a perspective view showing an embodiment of a partly cutaway diaper according to the present invention.

A disposable pull-on diaper 1 shown by FIG. 1 in a plan view as partially broken away comprises an absorbent core 2, a topsheet 3 overlying the absorbent core 2 and a backsheet 4 underlying the absorbent core 2. The diaper 1 has a front waist region 6 to cover the wearer's belly, a rear waist region 7 to cover the wearer's back and a crotch region 8 extending between these front and rear waist regions 6, 7 to cover the wearer's crotch. The front and rear waist regions 6, 7 are put flat together along respective pairs of their opposite side edges which are, in turn, joined together by means of adhesive spots intermittently arranged in their vertical directions so as to form a waist-opening 11 and a pair of leg-openings 12. The respective openings 11, 12 are provided along their peripheries with elastic member 13 for the waist-opening 11 and elastic members 14 for the leg-openings 12. These elastic members 13, 14 circumferentially extend between the topsheet 3 and the backsheet 4 and are secured under appropriate tension to the inner surface of at least one of these sheets 3, 4 by means of hot melt adhesive 16.

Figure 2A:
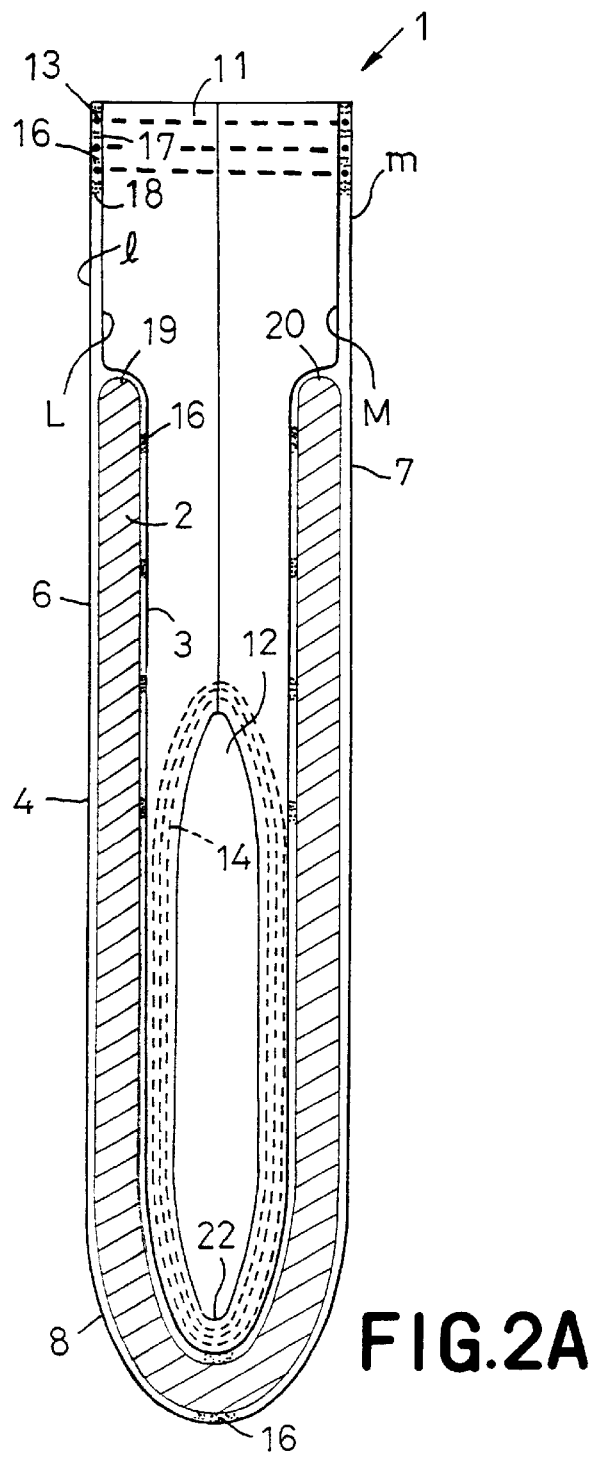
FIGS. 2A and 2B are sectional views taken along a line II—II in FIG. 1, showing the diaper with elastic members for leg-openings being in a stretched state FIG. 2A and with the elastic members being in a contracted state FIG. 2B.
Figure 2B:
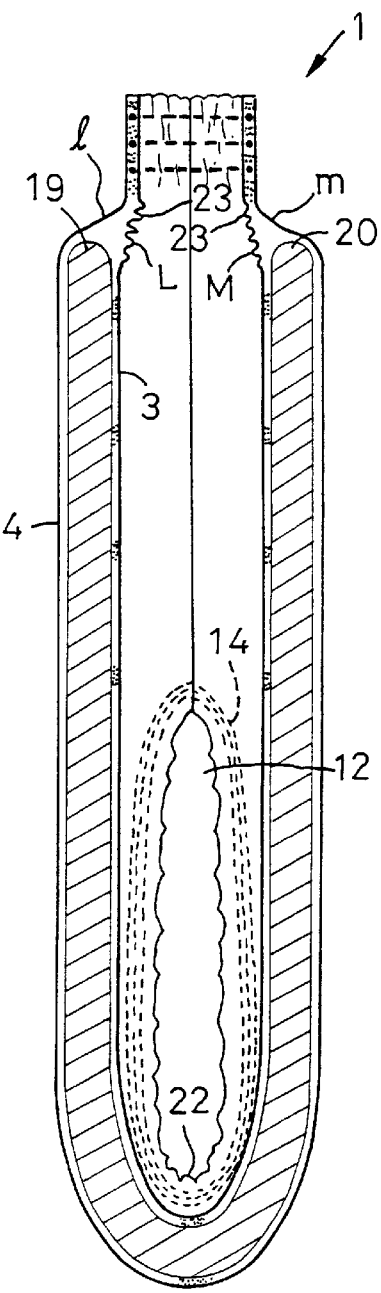

FIGS. 2A and 2B are sectional views taken along a center line II—II (See FIG. 1) bisecting a width of the diaper 1, showing the diaper 1 with both the elastic member 13 for the waist-opening and the elastic members 14 being in a stretched state as they are in FIG. 1 FIG. 2A and with these elastic members 13, 14 being in a contracted state FIG. 2B.

As will be apparent from FIG. 2 (A), the absorbent core 2 and the topsheet 3 are intermittently joined to each other by means of hot melt adhesive 16 arranged in the front and rear waist regions 6, 7 as well as in the crotch region 8 so that the absorbent core 2 has a movement thereof relative to the topsheet 3 restricted by the hot melt adhesive 16. On the other hand, the absorbent core 2 is movable relatively to the backsheet 4 in the front and rear waist regions 6, 7 because the absorbent core 2 and the backsheet 4 are not joined to each other in these front and rear waist regions 6, 7. However, it should be understood that, in the crotch region 8, the absorbent core 2 and the backsheet 4 may be or not joined to each other. According to the embodiment shown in FIGS. 2A and 2B, the absorbent core 2 and the backsheet 4 are joined to each other by means of hot melt adhesive 16 at the bottom of the crotch region 8. The topsheet 3 and the backsheet 4 are joined to each other by means of hot melt adhesive 16 along a peripheral edge 17 of the waist-opening 11. The peripheral edge 17 corresponds to a zone in which the elastic member 13 for the waist-opening 11 is secured to at least one of the topsheet 3 and the backsheet 4. The topsheet 3 and the backsheets 4 are not joined to each other in zones L, l, M, m defined between the lowermost level 18 of the peripheral edge 17 along which the topsheet 3 and the backsheet 4 are joined to each other and longitudinally opposite ends, i.e., front and rear ends 19, 20 of the absorbent core 2 so that these two sheets 3, 4 are free from each other in these zones. A total dimension of zones L, l, M, m is in a range of 10~150 mm, preferably 20~130 mm and more preferably 30~110 mm. It will be obviously understood that, along the substantially entire side edges of the topsheet 3 and the backsheet 4 and the zones in the vicinity of these side edges, the topsheet 3 and the backsheet 4 are joined to each other at the spots 9 intermittently arranged in their vertical directions or continuously joined to each other.

As will be apparent from FIG. 2(B), contraction of the elastic members 14 for the leg-openings 14 causes the lowermost portions 22 of the respective openings 12 to be lifted together with portions of the absorbent core 2 and the topsheet 3 and the backsheet 4 lying adjacent the lower most portions 22. Thereupon, the front and rear ends 19, 20 of the absorbent core 2 are also lifted and, in consequence, the zones L, M of the topsheet 3 are formed with fine gathers 23 while the backsheet 4 slightly slackens in its vertical direction. In this manner, the absorbent core 2 is free from any crookedness or the other deformation during its upward movement since none of factors obstruct the absorbent core 4 against its upward movement.

Figure 3:
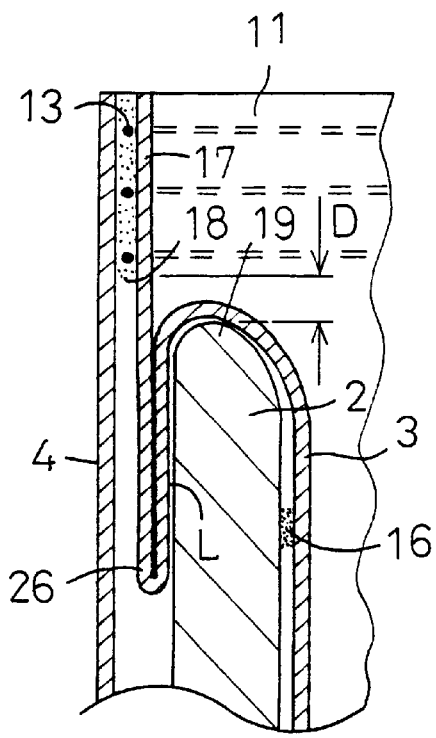
FIG. 3 is a fragmentary sectional view showing important parts in an alternative embodiment of the diaper according to the present invention.
Figure 4:
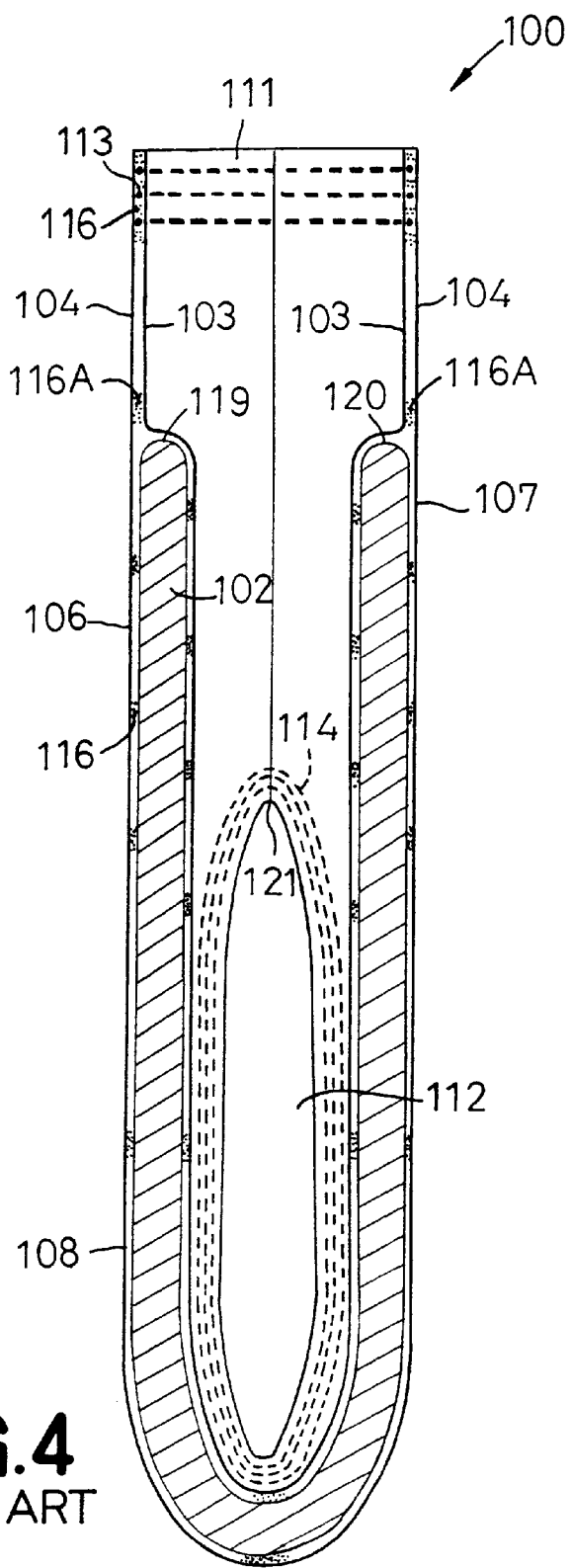
FIG. 4 is a view similar to FIG. 2 showing the diaper of prior art with the elastic members for the leg-openings being in a stretched state.
Figure 5:
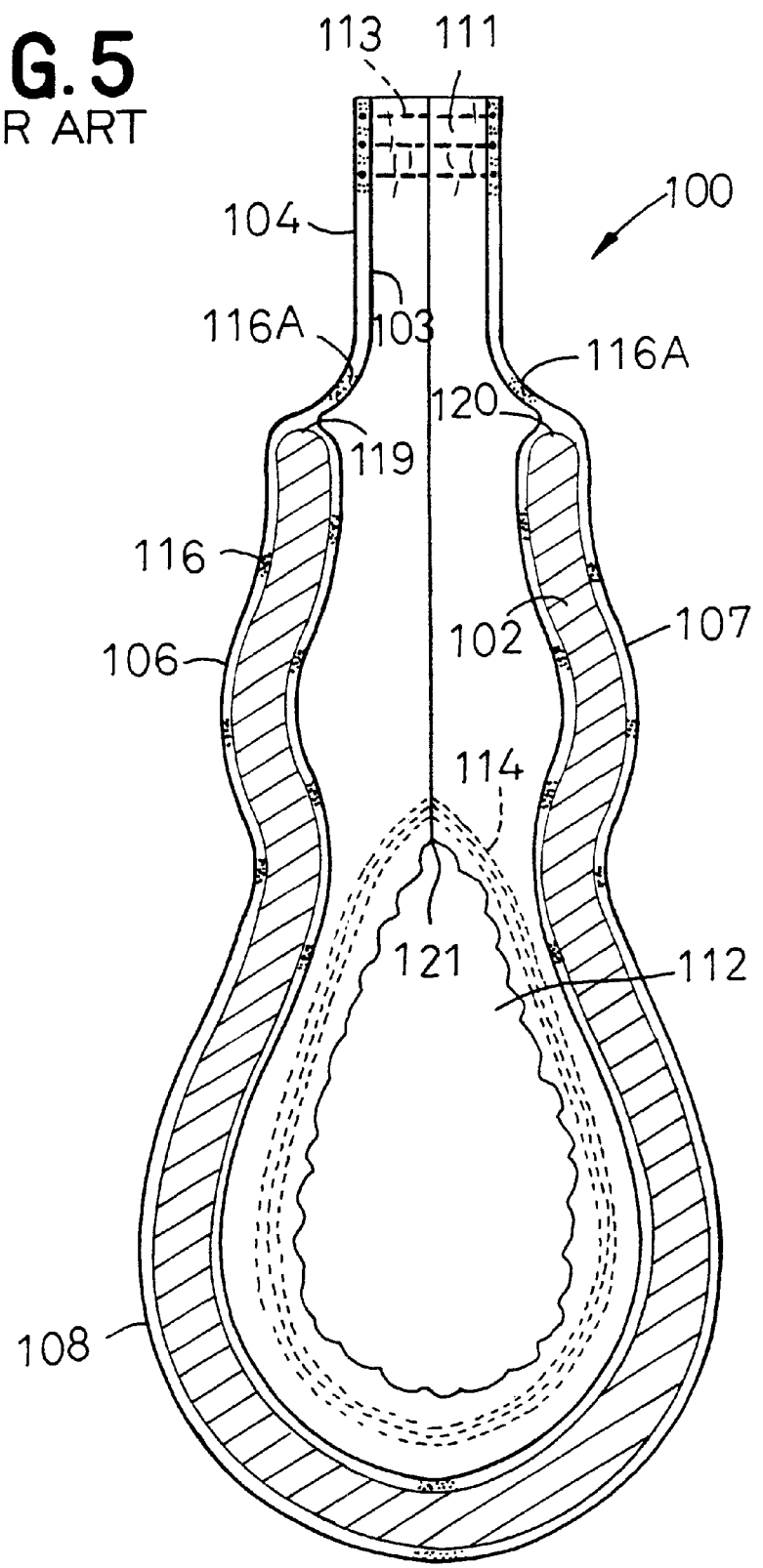
FIG. 5 is a view similar to FIG. 4 showing the diaper of prior art with the elastic members for the leg-openings being in a contracted state.

FIG. 3 is a view similar to FIG. 2(A), showing, in enlarged scale, the part corresponding to that as shown in FIG. 2(A) but modified according to an alternative embodiment of the present invention. According to the present embodiment, the portion L of the topsheet 3 extending between the lowermost level 18 of the waist-opening's peripheral edge 17 and the front end 19 of the absorbent core 2 is tucked between the absorbent core 2 and the backsheet 4, forming a pleat 26. The pleat 26 is bonded neither to the absorbent core 2 nor to the backsheet 4 so that the pleat 26 may be extended as the absorbent core 2 moved upward. Therefore nothing obstructs the upward movement of the absorbent core 2. Such embodiment can be adopted when a distance D between the lowermost level 18 of the peripheral edge 17 and the front end 19 of the absorbent core 2 is limited, for example, to a range of 0~30 mm. It should be understood that the portion L of the topsheet 3 (See FIG. 2) extending between the lowermost level 18 of the waist-opening's peripheral edge 17 and the front end 19 of the absorbent core 2 includes the pleat 26 extending from the lowermost level 18 to the front end 19. Such pleat 26 may be formed in the rear waist region 7 also.

To exploit the present invention, the topsheet 3 may comprise a liquid-pervious sheet as its portion destined to cover at least the absorbent core 2 and a substantially liquid-impervious sheet as its portion destined to extend outward beyond a peripheral edge of the absorbent core 2. As stock material for the backsheet 4, a liquid-impervious or substantially liquid-impervious sheet may be used. The liquid-pervious sheet may be selected from a group consisting of a nonwoven fabric, an aperture plastic film etc., and the liquid-impervious sheet may be selected from a group consisting of a plastic film, etc.

With the disposable pull-on diaper according to the present invention, contraction of as elastic members for the leg-openings causes the absorbent core to be freely moved upward without any crookedness of the absorbent core as the diaper of prior art has usually been the case. Accordingly, the absorbent core according to the present invention has no permanent crookedness formed thereon. Such absorbent core is substantially flat and allows the diaper to be compactly packaged. In addition, such absorbent core having no permanent crookedness or deformation contributes to improvement of the diaper's fitting to the wearer's body.

What is claimed is:

1. A disposable pull-on diaper comprising:

a front waist region;

a rear waist region;

a crotch region located between the front waist region and the rear waist region;

a liquid-absorbent core;

a liquid-pervious topsheet overlying said liquid-absorbent core; and a liquid-impervious backsheet underlying said liquid-absorbent core, said liquid-absorbent core extending across said crotch region into said front and rear waist regions and having front and rear ends, said front and rear waist regions being joined to each other along side edges thereof to form a waist-opening and a pair of leg-openings, said waist-opening and said pair of leg-openings each having peripheral edges, said front and rear waist regions including front and rear waist zones in which said front and rear ends of said liquid-absorbent core are movable longitudinally of said diaper, said waist-opening and leg-openings being provided with elastic members secured under tension thereto and extending circumferentially along said peripheral edges of said waist-opening and leg-openings, said liquid-pervious topsheet and said liquid-impervious backsheet being joined to each other along said peripheral edges of said waist-opening and said leg-openings, said liquid-absorbent core being joined to said liquid-pervious topsheet in said front and rear waist regions below said front and rear upper waist zones, said liquid-absorbent core also being joined to said liquid-pervious topsheet in said crotch region, said liquid-impervious backsheet being unattached to said liquid-absorbent core in said front and rear waist regions, said liquid-impervious backsheet further being unattached to said liquid-previous topsheet in said front and rear upper waist zones so that said liquid-absorbent core is freely movable relative to said liquid-impervious backsheet in said front and rear waist regions and so that said liquid-absorbent core is also freely movable in said front and rear upper waist zones relative to said liquid-pervious topsheet.

2. The diaper according to claim 1, wherein a portion of said liquid-pervious topsheet extending outward beyond any one of said front and rear ends of said liquid-absorbent core to said peripheral edge of said waist-opening is tucked between said liquid-absorbent core and said liquid-impervious backsheet.

3. A disposable pull-on diaper according to claim 1, wherein upper most joined portions between said liquid-absorbent core and said liquid-pervious topsheet in said front and rear waist regions are positioned at locations along said liquid-absorbent core that are lower than said front and rear ends thereof.

* * * * *